United States Patent [19]
Ligler et al.

[11] Patent Number: 5,965,305
[45] Date of Patent: Oct. 12, 1999

[54] METHOD FOR SURFACE MODIFICATION TO CREATE REGIONS RESISTANT TO ADSORPTION OF BIOMOLECULES

[75] Inventors: Frances S. Ligler, Potomac, Md.; Suresh Bhatia, Burke, Va.; Lisa C. Shriver-Lake, Silver Spring, Md.; Jacque Georger, Springfield; Jeff Calvert, Burke, both of Va.; Charles Dulcey, Washington, D.C.

[73] Assignees: The United States of America as represented by the Secretary of the Navy, Washington, D.C.; GEO-Centers, Inc., Newton Centre, Mass.

[21] Appl. No.: 08/367,888

[22] Filed: Jan. 3, 1995

Related U.S. Application Data

[60] Division of application No. 07/691,491, Apr. 25, 1991, Pat. No. 5,391,463, which is a continuation-in-part of application No. 07/182,123, Apr. 14, 1988, Pat. No. 5,079,600.

[51] Int. Cl.$^6$ ...................................................... G03C 3/00
[52] U.S. Cl. ........................ 430/17; 430/269; 430/271.1
[58] Field of Search .................... 430/17, 270.1, 430/269, 271.1, 272.1, 275.1; 427/558; 522/170

[56] References Cited

U.S. PATENT DOCUMENTS

| | | |
|---|---|---|
| 3,746,196 | 7/1973 | Sako et al. . |
| 3,907,564 | 9/1975 | Boardman et al. ..................... 430/270 |
| 4,103,064 | 7/1978 | McAlear et al. . |
| 4,103,073 | 7/1978 | McAlear et al. . |
| 4,562,157 | 12/1985 | Lowe et al. . |
| 4,587,169 | 5/1986 | Kistner ..................................... 428/413 |
| 4,587,203 | 5/1986 | Brault et al. ............................. 430/270 |
| 5,077,210 | 12/1991 | Eigler et al. .............................. 435/176 |
| 5,079,600 | 1/1992 | Schnur et al. . |
| 5,232,813 | 8/1993 | Okuno et al. ............................ 430/273 |
| 5,252,743 | 10/1993 | Barrett et al. ......................... 548/303.7 |
| 5,324,591 | 6/1994 | Georger et al. . |
| 5,391,463 | 2/1995 | Ligler et al. . |
| 5,510,628 | 4/1996 | Georger et al. . |

FOREIGN PATENT DOCUMENTS

| | | |
|---|---|---|
| 310413 | 4/1989 | European Pat. Off. . |
| 8704499 | 5/1989 | Sweden . |
| 465267 | 8/1991 | Sweden . |

OTHER PUBLICATIONS

Schoen et al, *Annual International Conference of the IEEE Engineering in Medicine and Biology Society*, vol. 12, No. 4, p. 1739 (1990).

Bhatia et al, *Analytical Biochemistry*, vol. 178, pp. 408–413 (1989).

H. Ahmad & M. Saleemuddin, *Analytical Biochemistry*, vol. 148, pp. 533–541 (1985).

B. Arkles et al, in *Silylated Surfaces*, D.E. Leyden, Ed., Gordon and Breach, N.Y., "Whole Cell and Cell Organelle Immobilization on Siliceous Surfaces" pp. 363–375.

*Primary Examiner*—Maria Nuzzolillo
*Assistant Examiner*—Laura Weiner
*Attorney, Agent, or Firm*—Oblon, Spivak, McClelland, Maier & Neustadt, P.C.

[57] ABSTRACT

Irradiating, with ultraviolet light, surfaces which contain thiol groups, epoxy groups, or vicinal diol groups, results in surfaces which exhibit a reduced adsorption of biomolecules. In the case of surfaces having thiol groups such irradiation also results in a reduced capacity for the bonding of heterobifunctional crosslinking reagents. Such irradiation may be carried out in a patternwise fashion to obtain patterned surfaces.

12 Claims, 2 Drawing Sheets

METHOD FOR SURFACE MODIFICATION TO CREATE REGIONS RESISTANT TO ADSORPTION OF BIOMOLECULES

This is a Division of application Ser. No. 07/691,491 filed on Apr. 25, 1991, now Pat. No. 5,391,463 which is a continuation-in-part of application Ser. No. 07/182,123, filed on Apr. 14, 1988 now Pat. No. 5,079,600.

BACKGROUND OF THE INVENTION

1. Field of the Invention

The present invention relates to a method of surface modification to create areas resistant to the adsorption of biomolecules and the patterned and unpatterned surfaces obtained by this method.

2. Discussion of the Background

Biosensor technology has opened the doors for the incorporation of a wide variety of organic molecules, particularly proteins, into optical and electronic devices. In addition, there is increasing recognition of the potential for integrating organic molecules, including biomolecules and biomimetics, into optoelectronic hardware for improved speed, memory, signal transition, and miniaturization. As more complex devices are envisioned, these relatively large molecules must be selectively attached to surfaces such as glass and silicon. Previous methods used for patterning of biomolecules on surfaces include ink jet printing, standard microlithography followed by etching or lift off to remove preattached proteins, and attachment to photoactivated regions of a film. The first two methods are laborious, slow, and tend to damage the biomolecules. The last method is problematic in that most biomolecules are relatively sticky and will adsorb to the nonactivated regions of a silane film as well as to the activated regions.

Lowe et al, U.S. Pat. No. 4,562,157, describe patterns of covalently attached biomolecules deposited on photoactivated portions of a silane film. However, the disclosed method does not overcome the problem of nonspecific attachment of biomolecules to unmodified portions of the silane film.

Schoen. P. E. et al, 12th Annual Meeting of the IEEE, Nov. 1–6, 1990, describe the deposition of proteins using thiol silane films and subsequent pattern generation using photolithography. However, the disclosed method does not overcome the difficulties of maintaining protein activity during the photolithography.

J. H. McAlear et al, U.S. Pat. Nos. 4,103,064 and 4,103,073 disclose the attachment of thick films of proteins and subsequent microlithographic patterning using standard resist technology. The drawbacks of this method include: (1) many steps are involved; (2) there is no covalent attachment between the protein and the substrate; (3) many resists entail the use of organic solvents such as diglyme that are known to denature proteins; (4) the development of many resists require the use of alkaline developers which may denature proteins; (5) the crosslinking agent glutaraldehyde is known to denature proteins; and (6) exposure of the protein to harmful radiation.

Bhatia. S. K. et al, *Anal. Biochem.*, 178, 408–413, 1989, describes the chemistry used for covalent attachment of biomolecules to a surface, utilizing heterobifunctional crosslinkers coupled to thiol silanes. This work does not demonstrate patterning of biomolecules.

A number of silane coating agents are known to reduce biomolecule adsorption (see: U.S. Pat. No. 3,746,196; and Arkles et al, in "Silylated Surfaces", D. Leyden, ed Gordon & Breach, NY (1980)).

Thus, there remains a need for a method of modifying surfaces to create areas which are resistant to the adsorption of biomolecules. There also remains a need for a method of producing surfaces which contain a patterned area or areas which are resistant to the adsorption of biomolecules. There also remains a need for surfaces produced by such methods. There also remains a need for a method for preparing patterned surfaces having areas which exhibit a reduced capacity to react with heterobifunctional crosslinking agents.

SUMMARY OF THE INVENTION

Accordingly, it is one object of the present invention to provide a novel method for modifying a surface to create a surface area exhibiting a resistance to biomolecule adsorption.

It is another object to provide a method for preparing a surface which contains a patterned area or areas which are resistant to biomolecule adsorption.

It is another object of the present invention to provide surfaces which exhibit a resistance to biomolecule adsorption.

It is another object of the present invention to provide surfaces which contain a patterned area or areas which are resistant to biomolecule adsorption.

It is another object of the present invention to provide a method for preparing surfaces which contain areas exhibiting a reduced capacity to react with heterobifunctional crosslinking reagents.

It is another object of the present invention to provide surfaces which contain a patterned area or areas which possess a reduced capacity to react with heterobifunctional crosslinking reagents.

It is another object of the present invention to provide a method for preparing surfaces which contain areas exhibiting a reduced capacity to react with heterobifunctional crosslinking reagents and a resistance to biomolecule adsorption.

It is another object of the present invention to provide surfaces which contain a patterned area or areas which exhibit a reduced capacity to react with heterobifunctional crosslinking reagents and exhibit a resistance to biomolecule adsorption.

These and other objects, which will become apparent during the following detailed description, have been achieved by the inventors' discovery that ultraviolet irradiation of a surface containing thiol groups, epoxy groups or vicinal diol groups results in a reduction in biomolecule adsorption. The irradiation of a surface containing thiol groups results in a reduced capacity for bonding heterobifunctional crosslinking reagents.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1A:
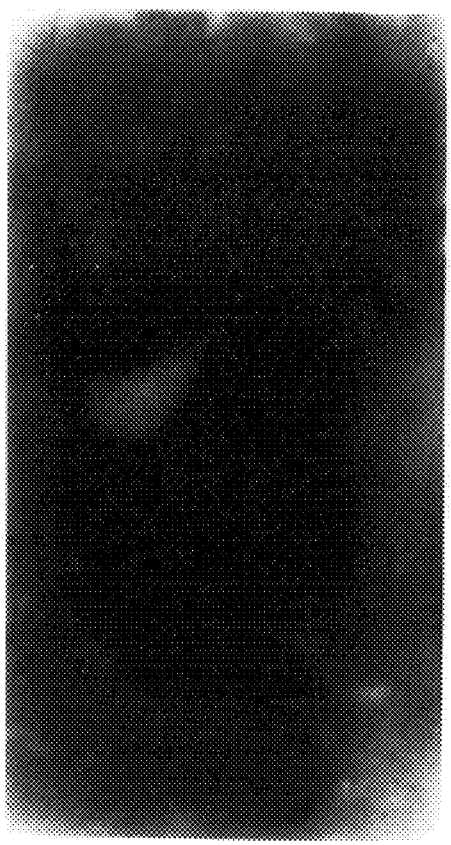
FIG. 1a is an autoradiograph illustrating the covalent attachment of $^{125}$I-labelled goat IgG to a surface first coated with mercaptopropyltrimethoxysilane and then treated with GMBS, without irradiation.

Thus, the present invention relates to a method for modifying surfaces by ultraviolet irradiation and the surfaces so obtained. The irradiation may be carried out using any suitable source of ultraviolet light, such as mercury lamps, excimer lasers and other sources described in U.S. patent application Ser. No. 07/182,123, Schnur et al, which is incorporated herein by reference.

The surface to be modified by the present method may be any which contains thiol groups, epoxy groups, or vicinal diol groups. These groups may be introduced onto a surface by a chemical modification step or may occur on the surface as a result of occurring in the material of which the surface is made. Examples of groups which are introduced onto a surface include those which occur in silane compounds which are deposited on a substrate as a self-assembling monolayer. Thus, a suitable substrate may be treated with compounds of the formulae

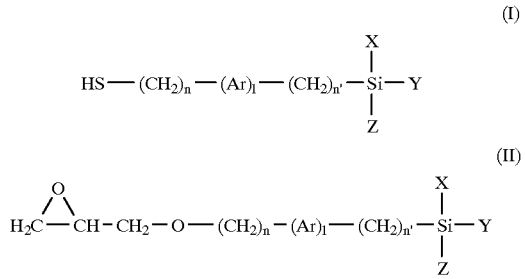

wherein Y, X, and Z are each independently $C_{1-4}$-alkyl, or $C_{1-4}$-alkoxy, provided that at least one of Y, X, and Z is $C_{1-4}$-alkoxy, Ar is aryl n is 1 to 20, preferably 2 to 20, most preferably 3, n' is 1 to 20, preferably 2 to 20, most preferably 3, l is 0 or 1, with the proviso that when l is 0, n' is 0.

The Compounds of formulae I and II may suitably be reacted with any substrate, which possesses functional groups that will react with a Si—OR (R=$C_{1-4}$-alkyl) group to result in the formation of a covalent bond between the Si atom in the compound of formulae I or II and the surface of the substrate. Examples of such substrates include glass, quartz, platinum, silicon nitride, germanium, polyvinyl phenol, or surfaces which may undergo chemical, photochemical or electrochemical modification to produce surface oxides.

The vicinal diol groups to be irradiated may be introduced onto a surface by hydrolyzing epoxy groups occurring on a surface as shown below:

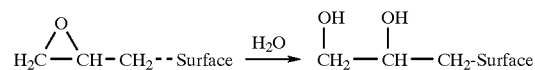

As discussed above, epoxy groups may be introduced onto a surface by treatment of a substrate with a compound of formula II.

Alternatively, the surface to be modified may be one which contains thiol groups, epoxy groups, or vicinal diol groups without chemical modification. Examples of such surfaces include poly(mercaptopropylmethylsilane). Polymers containing thiol functionalities may be produced by polymerizing, e.g. dimethoxy methyl mercaptopropylsilane. In addition, polymers containing repeating units having epoxyalkylsilicon or mercaptoalkylsilicon groups are commercially available (Petrarch Catalog, Bristol Pa., 1987). Alternatively, polymers containing alcohol functionalities such as polyvinyl phenol may be reacted with methoxy silanes containing thiol or epoxy functionalities to yield polymers with the desired functionalities. In all of these cases, the epoxy groups may be converted to diol groups as described above.

The present method may be carried out by irradiating an entire surface to result in a surface of which the entirety is resistant to biomolecule adsorption. Such a method may be desirable for the production of surfaces which will be exposed to environments containing biomolecules and which are desired to exhibit a resistance to fouling by biomolecule adsorption. Examples of such surfaces include those to be used in, e.g., glassware used in protein purification separation, blood bags, pipets, syringes, kidney dialysis tubing, implants, catheters, and lenses, including contact lenses.

Alternatively, the present method may be carried out by irradiating the surface in a patternwise manner to obtain a surface which contains a patterned area or areas which exhibit a resistance to biomolecule adsorption. Such patternwise irradiation may be carried by using any conventional technique, such as contact, proximity, direct laser writing, or projection printing. Such patterned surfaces are useful for biosensors, transducers (devices in which the detection is effected by the proximity of biomolecule to a transducer), construction of arrays of biomolecules, and implants, in which there are areas where biomolecule adsorption is desired and areas where biomolecule adsorption is not desired.

The exact amount of irradiation to which the surface should be exposed will depend on the identity of the functional group on the surface. Suitably, the surface is exposed to 0.001 Joules/cm$^2$ to 20 Joules/cm$^2$, preferably 0.01 Joules/cm$^2$ to 5 Joules/cm$^2$. Suitably, the surface is irradiated with light having a wavelength of 0.1 nm to 500 nm, preferably 120 nm to 400 nm of light. For any given light source, the amount of irradiation may be controlled by varying the duration of irradiation. For any particular functional group and any particular light source the preferred duration of irradiation may be easily determined by one of ordinary skill by using the methods described in the examples discussed below.

In the context of the present invention, the term biomolecule refers to any polypeptide (such as proteins, enzymes, antibodies, etc.), polysaccharide, or polynucleic acid. By the term "resistance to biomolecule adsorption" it is meant that the surface which has been exposed to the ultraviolet irradiation exhibits a reduction in the amount of a biomolecule adsorbed on the surface, when contacted with a medium containing biomolecules available for adsorption, as compared to the amount of biomolecules adsorbed on the same surface before ultraviolet irradiation.

In another aspect, the present method may be used to provide patterned and unpatterned surfaces which exhibit a reduced capacity for reacting with a heterobifunctional crosslinking reagent. By the term "reduced capacity for reacting with a heterobifunctional crosslinking reagent" it is meant that the surface which has been exposed to the ultraviolet irradiation exhibits a reduction in the amount of heterobifunctional crosslinking reagent bonding, when contacted with a medium containing a heterobifunctional crosslinking reagent, as compared to the amount of heterobifunctional crosslinking reagent bonded to the same surface before ultraviolet irradiation. Suitable examples of heterobifunctional crosslinking reagents are described in the Pierce Catalog, Rockford, Ill., 1991. It is preferred that when the surface being treated is one which contains thiol groups, the heterobifunctional crosslinking agent be one which contains thiol reactive groups (Bhatia et al, *Anal. Biochem.* vol. 178, pp. 408–413 (1989), which is incorporated herein by reference. Specific examples of heterobifunctional crosslinking reagents include N-δ-maleimidobutyryloxy succinimide ester (GMBS), N-succinimidyl-3-(2-pyridyldithio) propionate (SPDP), N-succinimidyl-(4-iodoacetyl) aminobenzoate (SIAB), and succinimidyl 4-(p-maleimidophenyl) butyrate (SMPB). In this manner the patternwise and unpatterned attachment of biomolecules via a heterobifunctional crosslinking reagent may be controlled. Thus, the present method encompasses methods for controlling the biomolecule attachment to a surface by covalent attachment as well as by physical adsorption.

In the experiments, described in the Examples, glass is used as the solid support. The surface is cleaned to create a hydroxylated oxide layer. A thiol, or glycidyl silane is covalently attached to the surface. Where it is desirable that adsorption of biomolecules to the entire surface be minimized (as in anti-fouling applications), the entire surface is irradiated with sufficient UV light, preferably below 200 nm. Where the object is to make patterns of biomolecules, a lithographic mask is placed over the surface and regions of the silane film are irradiated through the mask with sufficient light. After irradiation, the biomolecule can be attached by adsorption or by a crosslinker (such as those described in Bhatia et al, *Anal. Biochem.,* 1989) to the unirradiated regions. Unattached biomolecules are washed from the surface with a buffer compatible with maintaining the function of the biomolecule and of the device, preferably one which contains low concentrations of a nonionic detergent such as Triton X-100.

The results shown in Tables 1 and 2 demonstrate the effect of irradiation of various silane films on the adsorption of $^{125}$I-labelled IgG to the modified glass substrates. The films were deposited on glass and irradiated with a low-pressure mercury argon pen-lamp for 10 minutes per side at a distance of 3.5 cm. Under these conditions, the irradiated mercaptopropyltrimethoxy silane is more effective in preventing protein adsorption than a shorter dimethyl thiol-silane (mercaptomethyldimethylethoxy silane).

The addition of the heterobifunctional crosslinker N-gamma-maleimidobutyryloxy succinimide ester (GMBS), which links the amino-terminal groups of the IgG to the thiol group of the silane, did not increase the amount of IgG bound to the irradiated surface. This result suggests that the thiol groups are not available after irradiation.

Figure 2A:
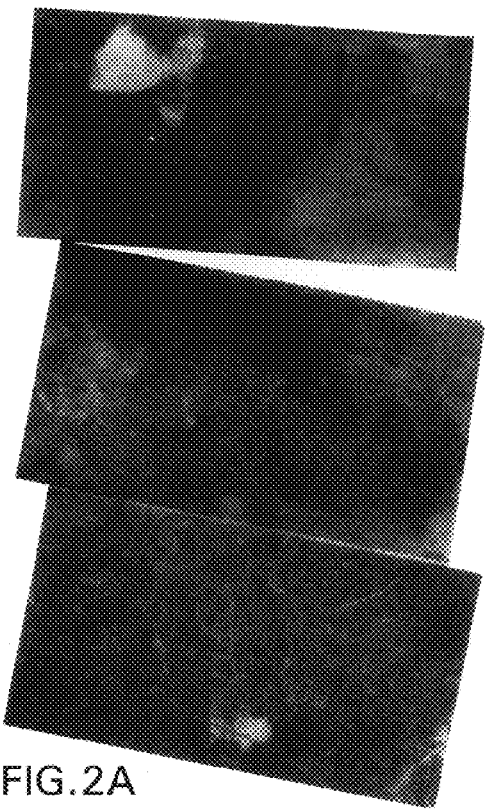
FIG. 2a shows an autoradiograph of three slides which were coated with mercaptopropyltrimethoxysilane, then treated with GMBS, then coated with unlabelled antibody and finally exposed to $^{125}$I-labelled antigen. The results indicate that the $^{125}$I-labelled antigen is bound over the entire surface.
Figure 2B:
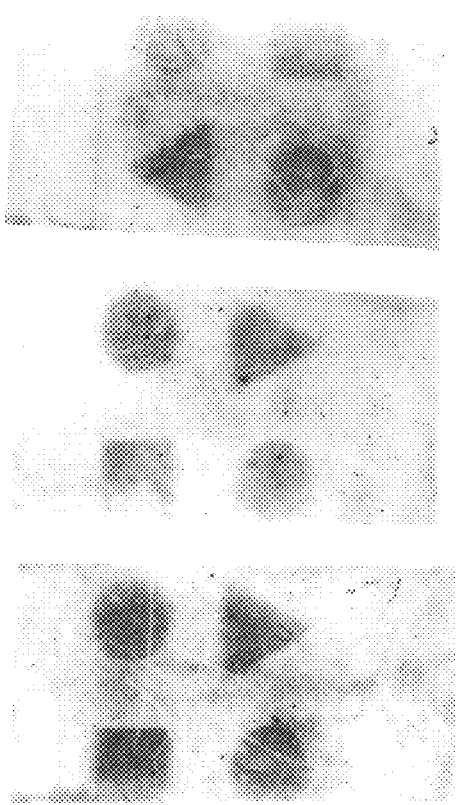
FIG. 2b shows an autoradiograph of three slides which were coated with mercaptopropyltrimethoxysilane, then irradiated through a mask, then treated with GMBS, then coated with unlabelled antibody, and finally exposed to $^{125}$I-labelled antigen. The dark areas are those which were covered by the mask, and the light areas are those which were exposed to irradiation.

FIG. 2 demonstrates the activity of antibodies immobilized on a silane film which has been patterned using a low pressure mercury argon pen-lamp. The glass surface was acid-cleaned, immersed in mercaptopropyltrimethoxy silane, dried, covered with a mask on one side, and exposed to UV light for ten minutes on each side. Next, the glass slide was immersed successively in the heterobifunctional crosslinker GMBS, anti-IgG antibody, phosphate-buffered saline, and radiolabeled IgG containing 2 mg/ml bovine serum albumen. Autoradiographs demonstrate the binding of significant amounts of the radiolabeled antigen to the antibody in the regions protected from UV light, but very little specific binding to regions exposed to UV light.

Thus, the present method enables the fabrication of (1) surfaces resistant to adsorption of biomolecules, and (2) surfaces with defined regions where biomolecules will and will not attach.

An advantage of the present method is that the irradiation procedure is conducive to making either high or low resolution patterns. Thus, the present method for making patterns of biomolecules is far simpler and faster than that of conventional etching or liftoff. The potential for damaging the biomolecules is also much lower if the biomolecules are added after all irradiation and patterning procedures. Furthermore, the present method specifically solves the problems associated with nonspecific adsorption of biomolecules to regions where they are not desired—a problem with the previously described photoactivation method of Lowe et al.

Having generally described this invention, a further understanding can be obtained by reference to certain specific examples which are provided herein for purposes of illustration only and are not intended to be limiting unless otherwise specified.

EXAMPLES

Methods:

The solid supports (glass cover slips) were cleaned before performing any experiment. The cleaning procedure was as follows. The glass cover slips were first immersed in a solution of methanol: concentrated hydrochloric acid (1:1) for 30 min followed by rinsing at least twice with doubly distilled water. These were then immersed in concentrated sulfuric acid for 30 min, rinsed several times with doubly distilled water, and boiled for 10 min in distilled water. Where dried cover slips were employed, these were drained onto low lint tissue paper and air dried.

Example 1

Silanization with 3-mercaptopropyltrimethoxysilane (MTS). Clean cover slips were placed in a glove bag under an inert atmosphere of nitrogen or argon. The slips were then treated with a 2% solution of MTS in anhydrous toluene while maintaining the inert atmosphere inside the glove bag for a 1 h period. The treated cover slips were rinsed with anhydrous toluene inside the glove bag and finally air dried in the hood. The silanized cover slips were used immediately for the subsequent steps.

Irradiation of the silanized surface. The cover slip was placed under the stabilized low pressure Hg(Ar) pen lamp at a distance of 3.5 cm, and exposed for 10 min on each side of the cover slip.

Adsorption of $^{125}$I-labeled IgG on non-irradiated and irradiated silanized surfaces was determined as follows. Irradiated and non-irradiated silanized cover slips were incubated separately with $^{125}$I-labeled goat IgG (0.05 mg/ml) in phosphate buffered saline (PBS, pH 7.4) at room temperature for 1 h. The slips were then washed with PBS and shaken with 0.1% Triton X-100 in PBS for 30 min. These were finally rinsed with PBS and the radioactivity was measured on a scintillation counter to quantitate the amounts of IgG adsorbed. The amount of protein adsorbed on non-irradiated the MTS-treated surface was $1.21\pm0.2$ ng/mm$^2$. On the irradiated surface, the amount was reduced to $0.17\pm0.02$ ng/mm$^2$, corresponding to only 14% of the IgG on the nonirradiated surface. This experiment demonstrates the effectiveness of irradiating a MTS film in reducing protein adsorption.

Example 2

The above experiment with MTS was repeated except that the UV irradiation was performed using an excimer laser with a monochromatic light at 193 nm. The substrate was exposed on both sides to 2 Joules/cm$^2$ from the laser. IgG adsorption was performed as in Example 1. The results demonstrate that $1.29\pm0.16$ ng/mm$^2$ IgG was adsorbed on the nonirradiated surface, while on the irradiated surface, the amount adsorbed was $0.18\pm0.006$ ng/mm$^2$. This also corresponds to 14% of the amount of IgG adsorbed on the nonirradiated surface. This result demonstrates the independence of the reduction in biomolecule adsorption with respect to the source of the UV light. This also demonstrates that exposing a surface treated with MTS to 2 J/cm$^2$ of 193 nm light will reduce the nonspecific adsorption of protein to 14%.

Example 3

Silanization with mercaptopropyldimethoxymethylsilane (MDMS) and mercaptomethyldimethylethoxysilane (MDS). The same procedure as employed with MTS in Example 1 was used for the silanizations except that the treatment with MDS was carried out for 2 h instead for 1 h. The UV irradiation and protein adsorption were performed as explained in Example 1. The amounts adsorbed on nonirradiated and irradiated MDMS treated surfaces were $1.7\pm0.14$ ng/mm$^2$ and $0.22\pm0.04$ ng/mm$^2$, respectively, demonstrating a 87% reduction in protein adsorption on irradiation. With MDS, the amounts were $0.46\pm0.05$ ng/mm$^2$ and $0.25\pm0.07$ ng/mm$^2$ on nonirradiated and irradiated surfaces, respectively (46% reduction).

The results for Examples 1 and 3 are tabulated in Table 1.

immediately prior to treatment. Clean cover slips from the boiling water rinse were transferred into this solution and allowed to stand in this solution for 15 min. The cover slips were then rinsed twice with anhydrous methanol and baked at 120° C. for 5 min.

UV irradiation and $^{125}$I-labeled goat IgG adsorption on these silanized cover slips were performed as explained in Example 1.

The amount of IgG adsorbed on the unirradiated ATS-treated surfaces was $0.67\pm0.07$ ng/mm$^2$. For the irradiated ATS-treated surfaces, the amount of protein adsorbed ranged from about 0.26 ng/mm$^2$ to about 0.64 ng/mm$^2$. With EDA, the amounts of protein adsorbed actually increased upon irradiation from $0.84\pm0.16$ ng/mm$^2$ on an unirradiated surface to $1.17\pm0.04$ ng/mm$^2$ on the irradiated surfaces. This comparative example demonstrates that although the monoaminosilane does reduce protein adsorption after irradiation the amount of protein remaining varies from 96% to 39% under similar conditions and that irradiation of a diaminosilane under these conditions results in increased nonspecific adsorption of proteins.

Example 5

Silanization with 3-glycidyloxypropyltrimethoxysilane (GOPS). Clean glass cover slips were exposed to water vapors and treated with a 4% solution of GOPS in toluene for 2 h inside a glove bag under inert atmosphere. The treated cover slips were rinsed with toluene and air dried before further use.

The epoxide ring was opened by treating the above slides with dilute hydrochloric acid (pH 3) for 30 min to generate a vicinal diol surface.

UV irradiation and goat IgG adsorption studies were performed on both epoxide and vicinal diol surfaces using the same conditions as described in Example 1. The nonirradiated epoxide surface adsorbed $0.28\pm0.08$ ng/mm$^2$ of IgG while on a similar irradiated surface, the amount was $0.21\pm0.07$ ng/mm$^2$. The vicinal diol surface adsorbed $0.3\pm0.1$ ng/mm$^2$ and $0.24\pm0.09$ ng/mm$^2$ of protein on non-irradiated and irradiated surfaces, respectively. This experiment demonstrates a reduction in protein adsorption on UV irradiation either on epoxy or on vicinal diol surface.

GOPS treated glass and other solid supports are employed in biochemical studies since such silanized surfaces are

TABLE 1

Protein Adsorption Studies on Different Thiol Silane Films With and Without Irradiation

| Silane* | Amount of goat IgG adsorbed | | % IgG left after irrad |
|---|---|---|---|
| | w/o irrad | w/irrad | |
| Mercaptopropyltrimethoxy (6) | 2137 + 348 ng ($1.21 \pm 0.2$ ng/mm$^2$) | 298 ± 36 ng ($0.17 \pm 0.02$ ng/mm$^2$) | 14 |
| Mercaptomethyldimethylethoxy (4) | 814 ± 94 ng ($0.46 \pm 0.05$ ng/mm$^2$) | 444 ± 125 ng ($0.25 \pm 0.07$ ng/mm$^2$) | 54 |
| Mercaptopropyldimethoxymethyl (3) | 3000 ± 250 ng ($1.7 \pm 0.14$ ng/mm$^2$) | 390 ± 67 ng ($0.22 \pm 0.04$ ng/mm$^2$) | 13 |

The number in parentheses indicates the number of experiments performed with each silane. Each experiment was performed with at least triplicate samples.

Comparative Example 4

Silanization with aminopropyltrimethoxysilane (ATS) and 3-(2-Aminoethyl-3-aminopropyl)trimethoxysilane (EDA). A 1% solution of ATS or EDA in methanol containing 0.001 M acetic acid and 5% distilled water was prepared known to keep the level of protein adsorption low. MTS treated surface upon UV irradiation (Example 1) gave similar or lower level of protein adsorption as compared to GOPS treated surface. This demonstrated the superiority of irradiated MTS surface in biochemical studies for low protein adsorption.

Example 6

Adsorption of bovine serum albumen (BSA) on nonirradiated and irradiated MTS treated surface. The procedure described in Example 1 was repeated on MTS treated cover slips except that $^{125}$I-labeled BSA was used instead of goat IgG. The amounts adsorbed were 0.74±0.12 ng/mm$^2$ and 0.19±0.05 ng/mm$^2$, on nonirradiated and irradiated surfaces, respectively (75% reduction). BSA is widely recognized as a protein which sticks to most surfaces. Yet, even such a sticky protein showed significantly reduced protein adsorption to the irradiated MTS-treated surface.

Example 7

Adsorption of glucose oxidase (an enzyme) on nonirradiated and irradiated MTS treated surface. The procedure described in Example 1 was repeated on MTS treated cover slips except that $^{125}$I-labeled glucose oxidase was used instead of goat IgG. On the irradiated surface, the adsorption of glucose oxidase was reduced to only 8%, as compared to the amount adsorbed on the nonirradiated surface. This experiment demonstrates the effectiveness of protein reduction process with an enzyme, such as glucose oxidase.

Example 8

Adsorption of $^{32}$P-labeled DNA on nonirradiated and irradiated MTS treated surface. The same procedure as explained with IgG protein in Example 1 was adopted with $^{32}$P-labeled DNA. The results revealed that 65% DNA was adsorbed on the irradiated surface compared to the nonirradiated surface. This experiment demonstrates a reduced adsorption of biomolecules other than proteins to the irradiated surfaces.

Example 9

Adsorption of proteins from Potomac River water on nonirradiated and irradiated MTS treated surfaces. MTS was coated on glass petri dishes and UV irradiation was performed with a pen lamp using the procedure described in Example 1. Equal amounts of water from the Potomac River were poured onto nonirradiated and irradiated MTS-treated glass petri dishes separately and allowed to stand for 1 h. Afterwards, the water was decanted, and the glass surface was rinsed with PBS.

A protein assay was performed using Coomassie Brilliant Blue dye following the procedure of H. Ahmad and M. Saleemuddin, *Analytical Biochemistry*, vol 148, pp. 533–541 (1985) on both the irradiated and nonirradiated samples.

The protein adsorbed on the silanized glass surface was fixed with 20% trichloroacetic acid for 15 min. After decanting the trichloroacetic acid, Coomassie blue solution (prepared by dissolving 100 mg of Coomassie Brilliant Blue G-250 in 100 ml of a solution of 10% (v/v) glacial acetic acid and 25% (v/v) isopropyl alcohol in distilled water, stirring it for 1 h at room temperature and filtering through a Whatman No. 1 filter paper) was placed onto both the nonirradiated and irradiated silanized glass surfaces for 30 min. The dye was decanted, and the glass surfaces were washed thoroughly with distilled water, until the washings were colorless. The dye on the glass surface was finally eluted with 2.9 ml of methanolic sodium hydroxide (0.1 M NaOH in 20% water and 80% methanol). The elutions were collected and acidified with 0.1 ml of 4 M hydrochloric acid. Absorbances of solutions were recorded at 604 nm. A parallel assay was performed simultaneously with known amounts of BSA on filter paper to obtain a standard curve. The calibration curve and fit value were obtained. The assay revealed that the amounts of proteins adsorbed on nonirradiated and irradiated surfaces were 11.7±1.3 ng/mm$^2$ and 5.4±0.1 ng/mm$^2$, respectively (54% reduction on irradiation). This experiment demonstrated the utility of using irradiated thiol films for reducing adsorption of complete mixture of proteins to objects exposed to the environment.

Example 10

Adsorption of proteins from human blood on nonirradiated and irradiated MTS treated surfaces. Example 9 was repeated using human blood instead of water from Potomac River. After treating each surface with 10 ml of blood, the silanized glass surface required several rinses with PBS. The assay was performed as explained in Example 7. The nonirradiated surface adsorbed 61.4±5.8 ng/mm$^2$ of proteins whereas the irradiated surface adsorbed 39.5±14.7 ng./mm$^2$ of proteins (36% reduction). This experiment demonstrates the utility of using irradiated surfaces on devices used for clinical procedures.

Example 11

For covalent immobilization of the IgG, the MTS-coated cover slips in Example 1 (both nonirradiated and irradiated), were exposed to the heterobifunctional crosslinker, N-gamna-maleimidobutyryloxy succinimide ester (GMBS, 2 mM in DMF/ethanol) for 1 h. After washing with PBS, the samples were incubated with $^{125}$I-labeled IgG as in Example 1, and the radioactivity was measured to quantitate the amounts attached. The amounts were, 0.96±0.1 ng/mn$^2$ and 0.15±0.02 ng/mm$^2$, respectively, on nonirradiated and irradiated surfaces (84% reduction). The residual protein adsorption was equivalent to that observed without GMBS, suggesting that no significant numbers of thiol groups were available after irradiation, for covalent attachment of protein. This demonstrates that patterned surfaces containing covalently attached protein areas next to areas that inhibit nonspecific adsorption can be produced.

Example 12

Example 11 was repeated with mercaptomethyldimethylethoxy silane (MDS) instead of MTS. The nonirradiated surface attached 0.54±0.11 ng/mm$^2$ of $^{125}$I-labeled IgG which was reduced to 0.22±0.03 ng/mm$^2$ on the irradiated surface (60% reduction).

The results for Examples 11 and 12 are tabulated in Table 2.

TABLE 2

Covalent Protein Attachment on Different Silane Films With and Without Irradiation

| Silane* | Amount of goat IgG Covalently Attached | | % IgG |
|---|---|---|---|
| | w/o irrad | w/irrad | after irrad. |
| Mercaptopropyltrimethoxy (6) | 1692 ± 175 ng<br>(0.96 ± 0.1 ng/mm$^2$) | 266 ± 36 ng<br>(0.15 ± 0.02 ng/mm$^2$) | 16 |
| Mercaptomethyldimethylethoxy (3 | 954 ± 198 ng<br>(0.54 ± 0.11 ng/mm$^2$) | 382 ± 52 ng<br>(0.22 ± 0.03 ng/mm$^2$) | 40 |

The number in parentheses indicates the number of experiments performed with each silane. Each experiment was performed with at least triplicate samples.

Example 13

Protein patterning after immobilization. For patterning a protein after immobilization, $^{125}$I-labeled goat IgG was covalently attached to the clean cover slips as mentioned in Example 11. After immobilization, a mask was placed on the samples. The samples were then irradiated with a Hg(Ar) pen lamp for 10 min on each side of the cover slip, washed with water, and exposed to x-ray film for autoradiography. In a separate experiment, the activity of the patterned protein was assessed. Unlabeled rabbit anti-goat IgG (antibody) was covalently immobilized and patterned as described above. The cover slip was finally incubated with $^{125}$I-labeled goat IgG (antigen) in the presence of BSA (2 mg/ml) as the blocking agent, and the radioactivity was measured.

The results demonstrate that although it is possible to obtain patterns of protein by irradiating after immobilization, the activity of the protein (antibody) is not reproducibly retained. Since the function of proteins may be reduced by irradiation, carrying out pattern formation prior to immobilization of biomolecules is preferred.

Example 14

Figure 1B:
FIG. 1b is an autoradiograph illustrating the covalent attachment of $^{125}$I-labelled protein to a surface first coated with mercaptopropyltrimethoxysilane and then treated with GMBS, with irradiation through a mask after the silane treatment and before the GMBS treatment. The dark areas are those which were covered by the mask, and the light areas are those which were exposed to the irradiation.

Patterning prior to protein immobilization. The glass cover slips treated with MTS were irradiated with UV light, in the presence of a mask, at a distance of 3.5 cm for 10 min on one side of the cover slip. The other side was irradiated without any mask. The cover slips both irradiated and nonirradiated were incubated with GMBS and radiolabeled protein and exposed to x-ray film. The exposure to x-ray film was carried out in a darkroom in the presence of an intensifier screen for 36–48 hrs. The results are shown in FIG. 1 and demonstrate that the protein may be covalently immobilized to the nonirradiated areas of the surface while irradiated areas are resistant to protein adsorption.

Example 15

Determination of the activity of patterned antibody. The cover slips were irradiated with a mask after MTS film formation and subsequently treated with the crosslinker GMBS. Then, unlabeled specific antibody (affinity purified rabbit anti-goat IgG) or control antibody (goat IgG) in PBS was covalently attached. The samples were shaken with 0.1% Triton X-100 for 30 min and rinsed with PBS. The supports were finally incubated with $^{125}$I-labeled antigen (goat IgG, 0.05 mg/ml) in PBS containing 2 mg/ml BSA as a blocking agent. After 1 h, the samples were washed with water and exposed to x-ray film for 36–48 hrs. The results are shown in FIG. 3. After obtaining a satisfactory autoradiograph, the radioactivity was determined. For a comparative study with patterned and unpatterned antibody, a parallel experiment was performed without any UV irradiation. This experiment demonstrates that a protein can be immobilized in well-defined patterns on surfaces without compromising protein function.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by: Letters Patent of the United States is:

1. A method for preparing a surface exhibiting reduced biomolecule adsorption, comprising:
   (i) forming a surface having thiol groups by reacting a substrate with a compound of formula (I)

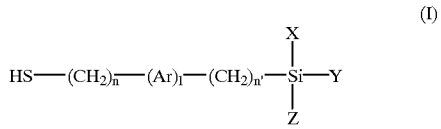

wherein X, Y, and Z are each independently $C_{1-4}$-alkyl or $C_{1-4}$-alkoxy, provided that at least one of X, Y, and Z is $C_{1-4}$-alkoxy, Ar is aryl, n is 1 to 20, n' is 1 to 20, l is 0 or 1, with the proviso that when l is 0, n' is 0; and (ii) irradiating said surface having thiol groups with ultraviolet light, to obtain an irradiated surface which exhibits a reduced amount of a biomolecule adsorbed on said irradiated surface when contacted with a medium containing a biomolecule as compared to the amount of biomolecule adsorbed to said surface having thiol groups when said surface having thiol groups is contacted with a medium containing a biomolecule, wherein said irradiating is carried out such that said surface having thiol groups is exposed to 0.001 Joules/cm$^2$ to 20 Joules/cm$^2$ of ultraviolet light.

2. The method of claim 1, wherein said irradiating comprises irradiating said surface having thiol groups in a patternwise fashion.

3. The method of claim 1, wherein n is 3, l is 0, and n' is 0.

4. The method of claim 1, wherein said irradiating is carried out such that said surface having thiol groups is exposed to 0.01 to 5 Joules/cm$^2$ of ultraviolet light.

5. The method of claim 1, wherein said substrate is selected from the group consisting of glass, quartz, platinum, silicon nitride, germanium, and polyvinyl phenol.

6. The method of claim 1, wherein said irradiating is carried out with a mercury lamp or an excimer laser.

7. A method for preparing a surface exhibiting reduced biomolecule adsorption, comprising:
   (i) forming a surface having vicinal diol groups by reacting a substrate with a compound of formula (II)

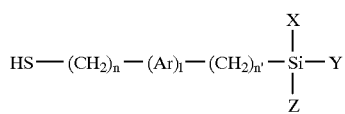 (I)

wherein X, Y, and Z are each independently $C_{1-4}$-alkyl or $C_{1-4}$-alkoxy, provided that at least one of X, Y, and Z is $C_{1-4}$-alkoxy, Ar is aryl, n is 1 to 20, n' is 1 to 20, l is 0 or 1, with the proviso that when l is 0, n' is 0, to obtain a surface having epoxy groups;

(ii) hydrolyzing said surface having epoxy groups to obtain a surface having vicinal diol groups; and (iii) irradiating said surface having vicinal diol groups with ultraviolet light, to obtain an irradiated surface which exhibits a reduced amount of a biomolecule adsorbed on said irradiated surface when contacted with a medium containing a biomolecule as compared to the amount of biomolecule adsorbed to said surface having vicinal diol groups when said surface having vicinal diol groups is contacted with a medium containing a biomolecule, wherein said irradiating is carried out such that said surface having vicinal diol groups is exposed to 0.001 Joules/cm$^2$ to 20 Joules/cm$^2$ of ultraviolet light.

8. The method of claim 7, wherein said irradiating comprises irradiating said surface having vicinal diol groups in a patternwise fashion.

9. The method of claim 7, wherein n is 3, l is 0, and n' is 0.

10. The method of claim 7, wherein said irradiating is carried out such that said surface having vicinal dial groups is exposed to 0.01 to 5 Joules/cm$^2$ of ultraviolet light.

11. The method of claim 7, wherein said substrate is selected from the group consisting of glass, quartz, platinum, silicon nitride, germanium, and polyvinyl phenol.

12. The method of claim 7, wherein said irradiating is carried out with a mercury lamp or an excimer laser.

* * * * *